United States Patent [19]

Higashi et al.

[11] Patent Number: 4,828,990
[45] Date of Patent: May 9, 1989

[54] METHOD FOR PURIFYING AN INTERFERON

[76] Inventors: Naoki Higashi, 8-12, Eirakuso 1-chome, Toyonaka-shi, Osaka; Shunjiro Sugimoto, 12-12, Mukomotocho 1-chome, Amagasaki-shi, Hyogo-ken; Masafumi Tsujimoto, 2-4-601, Minase 2-chome, Simamotocho, Mishima-gun, Osaka; Hounai Shirasawa, c/o Suntory Tondaryo 1-10, Himurocho 1-chome, Takatsuki-shi, Osaka; Tsutomu Okada, 38-2, Kinugasanishigoshonouchicho, Kita-ku, Kyoto-shi, Kyoto; Kazumori Yamamoto, 5-18-104, Wakayamadai 1-chome, Simamotocho, Mishima-gun, Osaka, all of Japan; Tattanahalli L. Nagabhushan, 3 Sunset La., Parshippany, N.J. 07054; Paul P. Trotta, 405 Park Ave., Rutherford, N.J. 07070

[21] Appl. No.: 908,707
[22] PCT Filed: Dec. 26, 1985
[86] PCT No.: PCT/JP85/00715
§ 371 Date: Oct. 10, 1986
§ 102(e) Date: Oct. 10, 1986
[87] PCT Pub. No.: WO86/04067
PCT Pub. Date: Jul. 17, 1986

[30] Foreign Application Priority Data
Dec. 27, 1984 [JP] Japan .................. 29-281376

[51] Int. Cl.⁴ .................. C12P 21/00; C07K 15/26; A61K 45/02
[52] U.S. Cl. .................. 435/68; 435/70; 435/811; 530/351; 424/85.5
[58] Field of Search .................. 435/68, 70; 424/85; 530/351

[56] References Cited

U.S. PATENT DOCUMENTS

| 4,266,024 | 5/1981 | Swetly et al. | 435/68 |
| 4,476,049 | 10/1984 | Kung | 424/85 |
| 4,751,078 | 6/1988 | Nogabhushar et al. | 424/85 |

FOREIGN PATENT DOCUMENTS

77670  4/1983  European Pat. Off. .

OTHER PUBLICATIONS

Chemical Abstracts, vol. 93, Abstract No. 90967t, 1980.
Biological Abstracts, vol. 73, Abstract No. 85856, 1982.
Chemical Abstracts; vol. 81, Abstract No. 87854a, 1974.

Primary Examiner—Blondel Hazel
Attorney, Agent, or Firm—Anita W. Magatti

[57] ABSTRACT

A method of purifying a polypeptide having a physiological activity such as one having interferon activities from a culture mixture of a microorganism obtained by a recombinant DNA technique and capable of producing the polypeptide is disclosed. The method comprises subjecting the cultured cells to extraction and purification in the presence of a salt of zinc or copper and polyethyleneimine thereby inhibiting decomposition and denaturation of the polypeptide. The extracted polypeptide can be further purified by column chromatographies using a column containing an anion exchange resin, column containing a cation exchange resin and column containing a gel filtration resin.

21 Claims, 7 Drawing Sheets

METHOD FOR PURIFYING AN INTERFERON

TECHNICAL FIELD

This invention relates to a method for purifying a physiologically active polypeptide produced by a recombinant DNA technology without denaturation or decomposition by proteases, more particularly, said polypeptide being produced by a microorganism transformed by a plasmid vector bearing a gene coding for a polypeptide having physiological activities. This Invention in particular provides an effective method for purifying a desired polypeptide from a culture mixture of a microorganism capable of producing a polypeptide having interferon activities, especially human immune (or gamma) interferon activities.

BACKGROUND ART

Interferon proteins have been classified into three types, alpha, beta and gamma (abbreviated to IFN-α, IFN-β and IFN-γ respectively) based on antigenic and structural differences. Gamma interferon has a number of characteristics that differentiate it from alpha and beta interferons. Among these differences are antigenic distinctiveness and greater activity with regard to immunoregulation and anti-tumor effects. Human gamma interferon (referred to herein as "h-IFN-γ") may be produced by T lymphocytes stimulated by mutagens or by antigens to which they are sensitized. It may also be obtained through cloning and expression techniques now well known to the art.

Recently, it has become possible by the progress in genetic engineering to produce many physiologically active polypeptides from microorganisms or animal cells, although these substances have been produced by separation and purification from an organism. However, it cannot yet be said that a method has been established for extracting and purifying the intended substance with a purity sufficient to be used for drugs and without causing denaturation or decomposition.

Gamma interferon-containing cells, however obtained, are collected and are disrupted by various means such as osmotic shock, ultrasonic vibration, grinding or high shear disruption and the disrupted cell-gamma interferon mixture is then processed to isolate the gamma interferon. The insoluble debris is separated by centrifugation and the gamma interferon-containing supernatant is collected for purification.

Although disclosure has been made of certain technology for such production methods, e.g. a method extracting and purifying the polypeptide produced by recombinant microorganism by using guanidine hydrochloride and urea (Japanese Patent Public Disclosure No. 161321/1984 and U.S. Pat. No. 4,476,049) and a purification method using a monoclonal antibody (Japanese Patent Public Disclosure No. 186995/1984), the intended substance is not always adequately purified without being subjected to denaturation and without its activity being lost.

European Patent Application 0,087,686 discloses a three-step process for purifying human immune interferions from the cell-free supernatant or extract from the crude interferon source. In the first step (for naturally occurring interferon), an affinity column, such as Concanavalin-A Sepharose is used, followed by chromatography on a carboxymethyl silica column using an increasing salt gradient and finally, on a silica gel permeation column. If sufficient purity is not obtained, concentration and chromatography on either the TSK or CM column is used.

European Patent Application 0,063,482 disclosed a purification process employing chromatographic methods using (1) Controlled Pore Glass beads; (2) Concanavalin-A Sepharose; (3) Heparin-Sepharose or Procion Red-agarose; and (4) gel filtration.

European Patent Applications 0,107,498 and 0,077,670 disclose a purification scheme employing (1) polyethyleneimine precipitation; (2) pH precipitation of bacterial proteins; (3) concentration and dialysis; (4) chromatography on (a) carboxymethyl cellulose; (b) a calcium phosphate gel; (c) a carboxymethyl cellulose; and (d) gel filtration resins.

These purification processes require a multitude of steps, cause degradation of the interferon by degradation or aggregation of the interferon molecule, or otherwise result in a gamma interferon product obtained in low yield or with low activity.

It goes without saying that a method for extracting and purifying the intended polypeptide from the culture mixture of the intended substance-producing microorganism without the activity of the intended substance being lost and without being accompanied by denaturation is important for such used as pharmaceuticals and that the establishment of such technology is useful from the viewpoint of industry.

Such a purification method has been particularly desired for interferon, the employment of which in pharmaceuticals is now proceeding. Interferons have anti-virus activity, but IFN-γ is expected to be useful as an anti-tumor agent and immune regulator because of its particularly strong cell growth inhibition. Furthermore, interferon activity has several specificities; for example, when interferon is used as a pharmaceutical, it is preferable to use interferon which originated from a human. Furthermore, it is desirable to establish processes for extracting and purifying interferon produced by genetic engineering.

Usually, in extracting and purifying a polypeptide obtained from recombinant microorganisms, cultured microorganisms are first killed by using a bactericide (a necessary process from the viewpoint of safety) and then the dead cells are disrupted and subsequently subjected to extraction. In these treatments, the intended polypeptide is sometimes denaturated and its activity may be lost. Furthermore, these treatments are apt to activate proteases included in the cells and sometimes decompose the intended polypeptide.

A method in which a protein denatured and solubilized with a denaturing agent such as urea or guanidine hydrochloride is extracted and the denaturing agent is removed in the course of purification has previously been disclosed for polypeptides purified from cells or recombinant microorganisms (as described before in Japanese Patent Public Disclosure No. 161321/1984, U.S. Pat. No. 4,476,049, etc.). However, it is difficult to safely obtain complete renaturation of the intended polypeptide even though the denaturing agents are removed. Therefore, this method is not preferred if the intended polypeptide is used as a pharmaceutical because, when the partially denatured polypeptide is mixed, it can become an antigen. On the other hand, in the purification method using a monoclonal antibody which has also been reported (as described before in Japanese Patent Public Disclosure No. 186995/1984, etc.), it can be thought that a denatured and undesirable polypeptide or a polymerized polypeptide such as dimer and trimer may be bonded to the monoclonal antibody, depending upon the antigenic determinant recognized with the monoclonal antibody used. Recently, a method for extracting h-IFN-γ produced by recombinant *Escherichia coli* in the presence of a protease inhibitor for the purpose of inhibiting decomposition of polypeptide with protease has been disclosed in the above mentioned U.S. Patent, but the guanidine hydrochloride used therein is also known as a protein denaturing agent (see, example, Japanese Patent Public Disclosure No. 161321/1984). It is therefore expected that, although the decomposition of polypeptide with protease can be inhibited, production of a denatured protein may well result.

It would be further desirable to (1) provide a purification scheme to separate gamma interferon from the cell debris of the disrupted cells in which the gamma interferon was produced; (2) separate gamma interferon from cell contaminants in high yields and with high purity and activity; (3) separate recombinant gamma interferon from cell contaminants; and (4) separate gamma interferon from cell contaminants without substantially degrading the interferon. The purification process described below is such a process.

DISCLOSURE OF INVENTION

The purification method of the present invention efficiently provides a polypeptide having the intended physiological activity in substantially pure form, inhibiting decomposition of the polypeptide with protease and avoiding the denaturation of the polypeptide. Furthermore, although the present invention will achieve the purification of a polypeptide having h-IFN-γ activity, the method of the present invention is also applicable to the extraction and purification of polypeptides other than h-IFN-γ, which have a site susceptible to protease decomposition, such as Arg-Lys and Arg-Arg, and are produced by recombinant microorganisms.

In the present invention, the above-described problems are solved by adding one or more salts of zinc or copper and polyethyleneimine (abbreviated to PEI below) in the extraction process. More specifically, the invention comprises suspending the culture cells of a recombinant microorganisms in a buffer solution containing one or more salts of zinc or copper, disrupting the cells, then adding PEI to the centrifuged supernatant, and subsequently subjecting it to a suitable purification process.

Various compounds which can be used as the salts of zinc or copper include zinc chloride, zinc sulfate, zinc acetate, zinc acetylacetonate, and copper sulfate, but zinc chloride, zinc acetate and copper sulfate are preferred. There are differences in the optimum concentration of salt depending on the peptide-producing strain, but it is generally in the range of 0.5-5 mM, more preferably 1-3 mM in the case of zinc salts, and 0.01-3 mM, more preferably 0.25-1 mM in the case of copper salt.

These salts are mixed with a buffer solution in the above-described concentration, the culture cells are suspended in the resulting solution and then disrupted, and the supernatant is obtained by centrifugation. PEI is added to the supernatant to achieve a final concentration of 0.5-1.1%. The addition of PEI also functions to precipitate a considerable amount of impure proteins. After PEI addition, the supernatant is allowed to stand at a low temperature, for example about 4° C. After centrifugation to remove the precipitates, the desired substance is purified by a conventional method. The purification can be conveniently carried out by combining several columns and dialyses. In some cases, salting out may be involved in th process. Specific embodiments will be explained below in the Examples.

Prior to the present application, there was a report about the addition of a zinc salt to the culture medium in IFN-β production with a view to increasing productivity (Japanese Patent Public Disclosure No. 146597/1984). That report was however intended to increase production in titer during the cultivation and did not describe the addition of the salt together with PEI in the extracting step, as in the present invention. With regard to the use of copper compounds in the purification process, an example of the use of a copper-chelate resin column was reported in Japanese Patent Public Disclosure No. 167597/1984. However, that invention related to a purification method for a preliminarily purified IFN solution. Previous reports such as these above inventions are essentially different from the present invention which is characterized by the addition of the salts in the extraction stage for the purpose of purification without causing denaturation or decomposition of a protein throughout. Another object of the present invention is to provide a substantially pure polypeptide having h-IFN-γ activity which can be obtained by the method of purification and extraction of the present invention.

The construction of W3110/pIN5T4 which is one of the stains capable of producing a polypeptide having h-IFN-γ activity is disclosed in European Patent Application 0,134,673. The polypeptide produced by that strain is called GIF146 and is represented by the following amino acid sequence (I).

| 1 | | | | | | | | | 10 |
|---|---|---|---|---|---|---|---|---|---|
| Cys | Tyr | Cys | Gln | Asp | Pro | Tyr | Val | Lys | Glu |
| | | | | | | | | | 20 |
| Ala | Glu | Asn | Leu | Lys | Lys | Tyr | Phe | Asn | Ala |
| | | | | | | | | | 30 |
| Gly | His | Ser | Asp | Val | Ala | Asp | Asn | Gly | Thr |
| | | | | | | | | | 40 |
| Leu | Phe | Leu | Gly | Ile | Leu | Lys | Asn | Trp | Lys |
| | | | | | | | | | 50 |
| Glu | Glu | Ser | Asp | Arg | Lys | Ile | Met | Gln | Ser |
| | | | | | | | | | 60 |
| Gln | Ile | Val | Ser | Phe | Tyr | Phe | Lys | Lue | Phe |
| | | | | | | | | | 70 |
| Lys | Asn | Phe | Lys | Asp | Asp | Gln | Ser | Ile | Gln |
| | | | | | | | | | 80 |
| Lys | Ser | Val | Glu | Thr | Ile | Lys | Glu | Asp | Met |
| | | | | | | | | | 90 |
| Asn | Val | Lys | Phe | Phe | Asn | Ser | Asn | Lys | Lys |
| | | | | | | | | | 100 |
| Lys | Arg | Asp | Asp | Phe | Glu | Lys | Leu | Thr | Asn |
| | | | | | | | | | 110 |
| Tyr | Ser | Val | Thr | Asp | Leu | Asn | Val | Gln | Arg |
| | | | | | | | | | 120 |
| Lys | Als | Ile | His | Glu | Leu | Ile | Gln | Val | Met |
| | | | | | | | | | 130 |
| Ala | Glu | Leu | Ser | Pro | Ala | Ala | Lys | Thr | Gly |
| | | | | | | | | | 140 |
| Lys | Arg | Lys | Arg | Ser | Gln | Met | Leu | Phe | Arg |
| | | | | | | 146 | | | |
| Gly | Arg | Arg | Ala | Ser | Gln | | | | (I) |

The GIF146-producing strain is *Escherichia coli* W3110 transformed by a plasmid vector bearing a DNA fragment coding for the above-described GIF146 and represented by the DNA sequence (II).

| | | | | | | | | |
|---|---|---|---|---|---|---|---|---|
| TGC | TAC | TGC | CAG | GAC | CCA | TAC | GTG | AAG | GAA |
| ACG | ATG | ACG | GTC | CTG | GGT | ATG | CAC | TTC | CTT |
| GCT | GAA | AAC | CTG | AAG | AAA | TAC | TTC | AAC | GCT |
| CGA | CTT | TTG | GAC | TTC | TTT | ATG | AAG | TTG | CGA |
| GGT | CAT | TCT | GAC | GTT | GCT | GAC | AAC | GGT | ACT |
| CCA | GTA | AGA | CTG | CAA | CGA | CTG | TTG | CCA | TGA |
| CTG | TTC | CTG | GGT | ATC | CTG | AAA | AAC | TGG | AAA |
| GAC | AAG | GAC | CCA | TAG | GAC | TTT | TTG | ACC | TTT |
| GAA | GAA | TCT | GAC | CGT | AAA | ATC | ATG | CAG | TCT |
| CTT | CTT | AGA | CTG | GCA | TTT | TAG | TAC | GTC | AGA |
| CAG | ATC | GTT | TCT | TTC | TAC | TTC | AAG | CTG | TTC |
| GTC | TAG | CAA | AGA | AAG | ATG | AAG | TTC | GAC | AAG |
| AAA | AAC | TTC | AAG | GAC | GAC | CAG | TCT | ATC | CAG |
| TTT | TTG | AAG | TTC | CTG | CTG | GTC | AGA | TAG | GTC |
| AAA | TCT | GTT | GAA | ACT | ATC | AAG | GAA | GAC | ATG |
| TTT | AGA | CAA | CTT | TGA | TAG | TTC | CTT | CTG | TAC |
| AAC | GTT | AAG | TTC | TTC | AAC | TCT | AAC | AAG | AAA |
| TTG | CAA | TTC | AAG | AAG | TTG | AGA | TTG | TTC | TTT |
| AAG | CGT | GAC | GAC | TTC | GAA | AAG | CTT | ACT | AAC |
| TTC | GCA | CTG | CTG | AAG | CTT | TTC | GAA | TGA | TTG |
| TAC | TCT | GTT | ACT | GAC | CTT | AAT | GTA | CAG | CGT |
| ATG | AGA | CAA | TGA | CTG | GAA | TTA | CAT | GTC | GCA |
| AAA | GCT | ATC | CAT | GAA | CTG | ATC | CAG | GTT | ATG |
| TTT | CGA | TAG | GTA | CTT | GAC | TAG | GTC | CAA | TAC |
| GCT | GAA | CTG | TCC | CCG | GCT | GCT | AAA | ACT | GGT |
| CGA | CTT | GAC | AGG | GGC | CGA | CGA | TTT | TGA | CCA |
| AAG | CGT | AAA | AGA | TCT | CAG | ATG | CTG | TTC | CGT |
| TTC | GCA | TTT | TCT | AGA | GTC | TAC | GAC | AAC | GCA |
| GGT | CGT | CGT | GCT | TCT | CAG | TAA | | | |
| CCA | GCA | GCA | CGA | AGA | GTC | ATT | | | (II) |

On the other hand, the strain (W3110/pIN5T4N143) capable of producing a polypeptide having h-IFN-γ activity and represented by the following amino acid sequence (III) can be produced as explained below with reference to Examples. This polypeptide is referred to as GIF143 hereunder.

*

| | | | | | | | | | |
|---|---|---|---|---|---|---|---|---|---|
| Gln | Asp | Pro | Tyr | Val | Lys | Glu | Ala | Glu | Asn |
| Leu | Lys | Lys | Tyr | Phe | Asn | Ala | Gly | His | Ser |
| Asp | Val | Ala | Asp | Asn | Gly | Thr | Leu | Phe | Leu |
| Gly | Ile | Leu | Lys | Asn | Trp | Lys | Glu | Glu | Ser |
| Asp | Arg | Lys | Ile | Met | Gln | Ser | Gln | Ile | Val |
| Ser | Phe | Tyr | Phe | Lys | Leu | Phe | Lys | Asn | Phe |
| Lys | Asp | Asp | Gln | Ser | Ile | Gln | Lys | Ser | Val |

-continued

| | | | | | | | | | |
|---|---|---|---|---|---|---|---|---|---|
| Glu | Thr | Ile | Lys | Glu | Asp | Met | Asn | Val | Lys |
| Phe | Phe | Asn | Ser | Asn | Lys | Lys | Lys | Arg | Asp |
| Asp | Phe | Glu | Lys | Leu | Thr | Asn | Tyr | Ser | Val |
| Thr | Asp | Leu | Asn | Val | Gln | Arg | Lys | Ala | Ile |
| His | Glu | Leu | Ile | Gln | Val | Met | Ala | Glu | Leu |
| Ser | Pro | Ala | Ala | Lys | Thr | Gly | Lys | Arg | Lys |
| Arg | Ser | Gln | Met | Leu | Phe | Arg | Gly | Arg | Arg |
| Ala | Ser | Gln | | | | | | | (III) |

In this amino acid sequence, Gln* represents Gln or p-Gln.

Furthermore, the DNA fragment shown by the following DNA sequence coding for the polypeptide (GIF143) may be used for production of the intended plasmid vector.

| | | | | | | | | |
|---|---|---|---|---|---|---|---|---|
| CAG | GAC | CCA | TAC | GTG | AAG | GAA | GCT | GAA | AAC |
| GTC | CTG | GGT | ATG | CAC | TTC | CTT | CGA | CTT | TTG |
| CTG | AAG | AAA | TAC | TTC | AAC | GCT | GGT | CAT | TCT |
| GAC | TTC | TTT | ATG | AAG | TTG | CGA | CCA | GTA | AGA |
| GAC | GTT | GCT | GAC | AAC | GGT | ACT | CTG | TTC | CTG |
| CTG | CAA | CGA | CTG | TTG | CCA | TGA | CAA | AAG | GAC |
| GGT | ATC | CTG | AAA | AAC | TGG | AAA | GAA | GAA | TCT |
| CCA | TAG | GAC | TTT | TTG | ACC | TTT | CTT | CTT | AGA |
| GAC | CGT | AAA | ATC | ATG | CAG | TCT | CAG | ATC | GTT |
| CTG | GCA | TTT | TAG | TAC | GTC | AGA | GTC | TAG | CAA |
| TCT | TTC | TAC | TTC | AAG | CTG | TTC | AAA | AAC | TTC |
| AGA | AAG | ATG | AAG | TTC | GAC | AAG | TTT | TTG | AAG |
| AAG | GAC | GAC | CAG | TCT | ATC | CAG | AAA | TCT | GTT |
| TTC | CTG | CTG | GTC | AGA | TAG | GTC | TTT | AGA | CAA |
| GAA | ACT | ATC | AAG | GAA | GAC | ATG | AAC | GTT | AAG |
| CTT | TGA | TAG | TTC | CTT | CTG | TAC | TTG | CAA | TTC |
| TTC | TTC | AAC | TCT | AAC | AAG | AAA | AAG | CGT | GAC |
| AAG | AAG | TTG | AGA | TTG | TTC | TTT | TTC | GCA | CTG |
| GAC | TTC | GAA | AAG | CTT | ACT | AAC | TAC | TCT | GTT |
| CTG | AAG | CTT | TTC | GAA | TGA | TTG | ATG | AGA | CAA |
| ACT | GAC | CTT | AAT | GTA | CAG | CGT | AAA | GCT | ATC |
| TGA | CTG | GAA | TTA | CAT | GTC | GCA | TTT | CGA | TAG |
| CAT | GAA | CTG | ATC | CAG | GTT | ATG | GCT | GAA | CTG |
| GTA | CTT | GAC | TAG | GTC | CAA | TAC | CGA | CTT | GAC |
| TCC | CCG | GCT | GCT | AAA | ACT | GGT | AAG | CGT | AAA |
| AGG | GGC | CGA | CGA | TTT | TGA | CCA | TTC | GCA | TTT |
| AGA | TCT | CAG | ATG | CTG | TTC | CGT | GGT | CGT | CGT |
| TCT | AGA | GTC | TAC | GAC | AAG | GCA | CCA | GCA | GCA |
| GCT | TCT | CAG | TAA | | | | | | |

| | | | |
|---|---|---|---|
| CGA | AGA | GTC | ATT |

Figure 1:
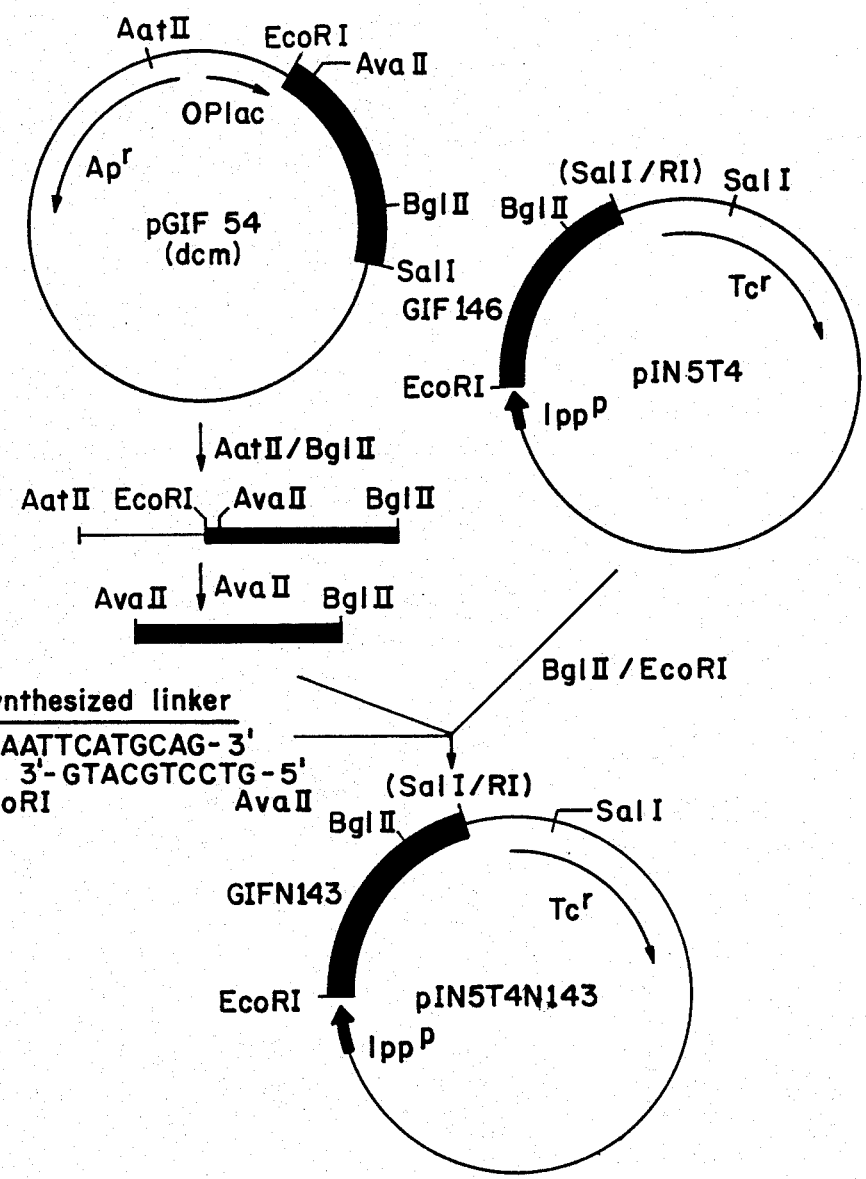
FIG. 1 is a figure illustrating construction scheme of plasmid vector pIN5T4N143 used for transformation of Escherichia coli to produce GIF143 which will be purified by the method of the present invention.
Figure 2:
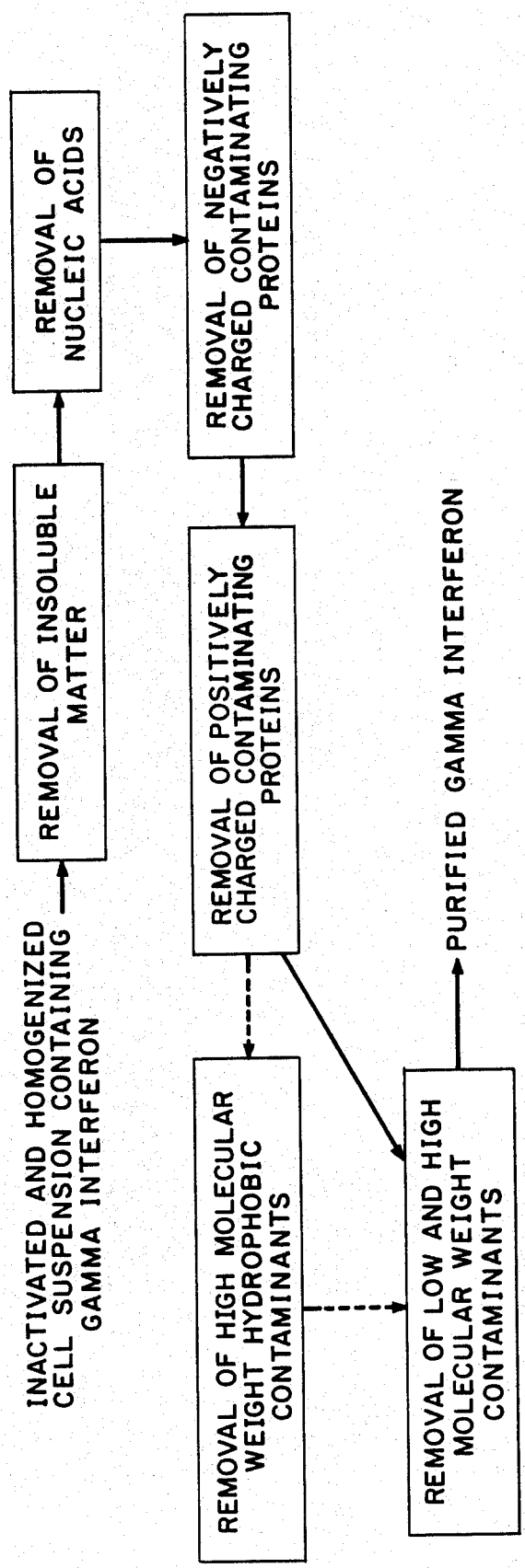
FIG. 2 is a flow diagram of a preferred embodiment of the gamma interferon purification process of the present invention.
Figure 3:
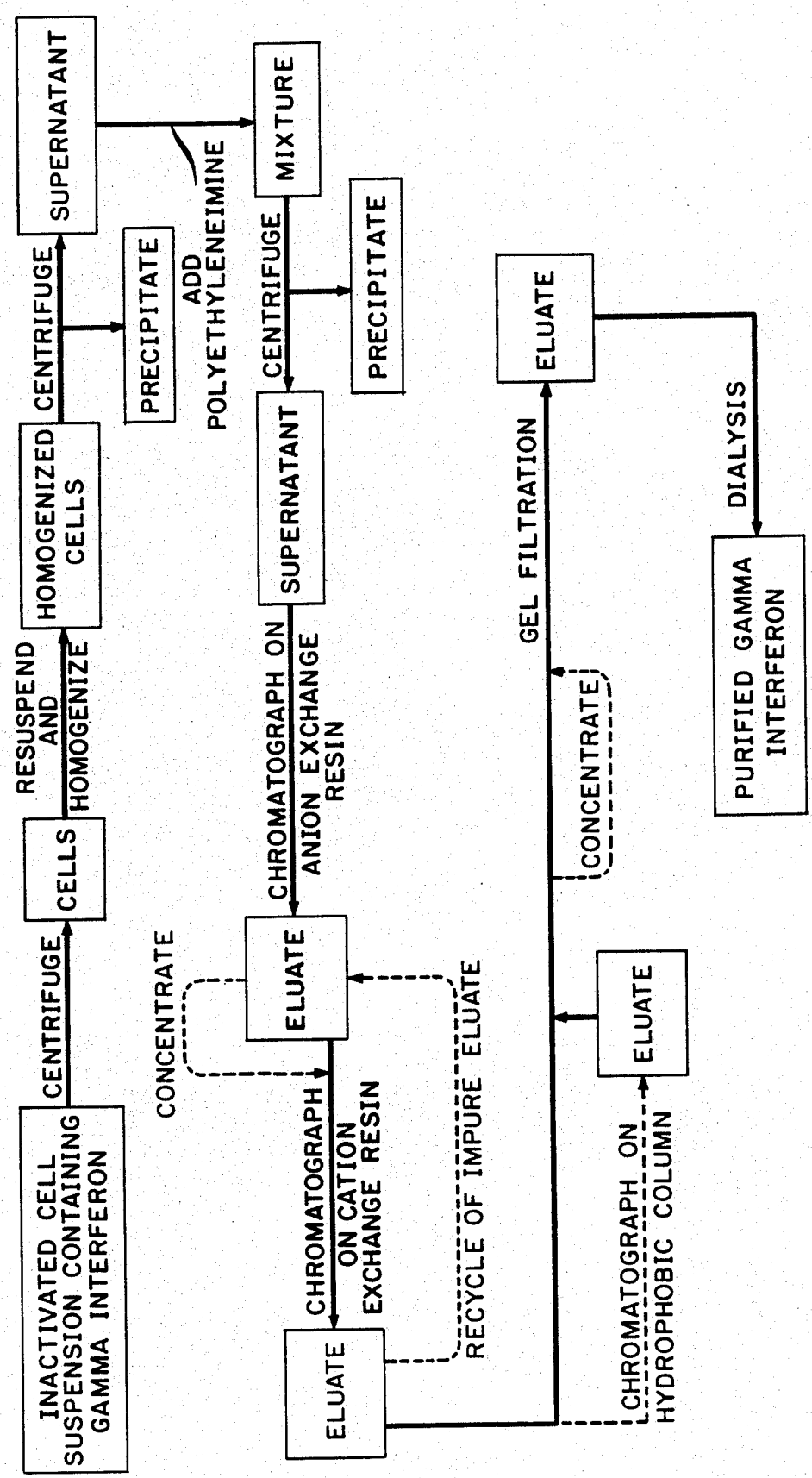
FIG. 3 is a flow diagram of a more preferred embodiment of this purification process showing primarily chromatographic purification means.
Figure 4:
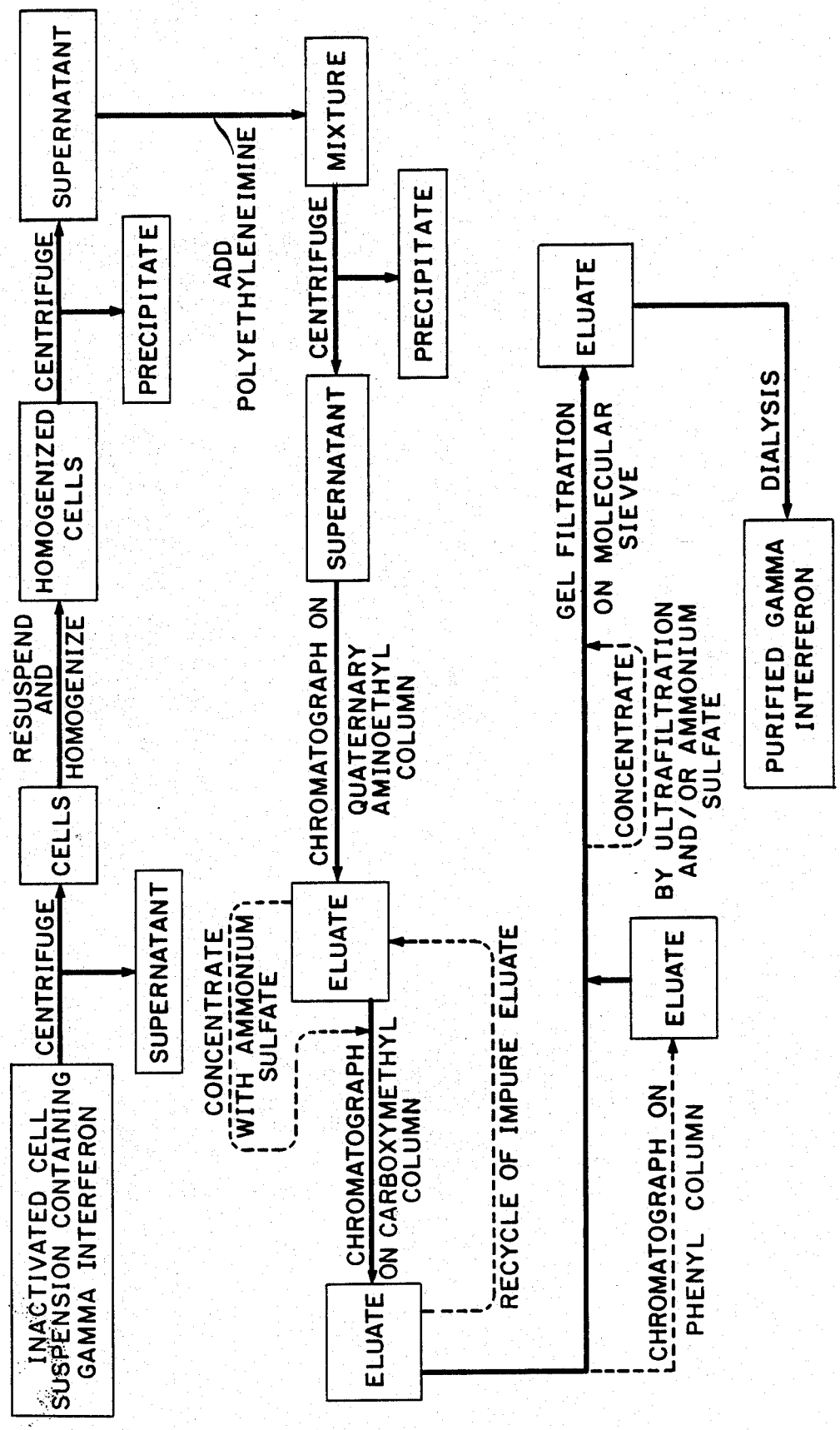
FIG. 4 is a flow diagram of a particularly preferred embodiment of the present invention.

The production is explained with reference to FIG. 1, in which the DNA fragment obtained by AatII and BglII digestion of pGIF54, which is essentially the same plasmid as pGIF4 disclosed in Japanese Patent Public Disclosure No. 201995/1983, is further treated with AvaII to obtain an AvaII-BglII DNA fragment as shown in FIG. 1. Then, the intended plasmid pIN5T4N143 is obtained by inserting in the presence of a DNA ligase a synthetic linker DNA fragment represented by

5'—AATTCATGCAG—3'

3'—GTACGTCCTG—5' between an AvaII site of the AvaII-BglII fragment above and an EcoRI site of a longer DNA fragment bearing a tetracycline resistant gene (TC$^r$) which is obtained by treating pIN5T4 (disclosed in European Patent Application 0,134,673) with BglII and EcoRI. The resulting plasmid contains a gene coding for a polypeptide GIF143 corresponding to GIF146 from which a sequence of 3 amino acid residues, i.e. Cys-Tyr-Cys, at the N-end of GIF146 is eliminated. Subsequently, a host (E. coli W3110) is transformed with the plasmid according to a conventional method to obtain a GIF-producing transformed Escherichia coli (W3110/pIN5T4N143).

In all figures, the purification process starts with the removal of nucleic acids from the supernatant resulting from centrifugation of homogenized gamma interferon-containing cells, prior stes being shown for clarity but not being part of the present invention.

Although a purification will be described by using zinc chloride as the salt of zinc in the Examples, the invention is not limited to this salt. Salts of zinc such as zinc sulfate and zinc acetate and salts of copper such as copper sulfate are also desirably used. Table I shows the protease-inhibition effects of various metallic salt compounds, which were investigated by disrupting cells of the recombinant bacteria in buffer solutions containing 1 mM or 0.2 mM of the metallic compound and measuring the stability of a polypeptide having h-IFN-γ activity contained in the supernatant liquid as an indicator of the effects. As indicated in Table I, it was found that zinc sulfate, zinc acetate, zinc acetylacetonate and copper sulfate provide the desired effects as well as zinc chloride.

TABLE I

Protease decomposition-inhibiting effect upon polypeptide by addition of Zn, Cu and other metal salts

| Metal Salt | Decomposition-inhibiting effect on polypeptide | |
|---|---|---|
| | 1 mM | 0.2 mM |
| None | — | — |
| Zinc chloride | + | — |
| Zinc sulfate | + | — |
| Zinc acetate | + | — |
| Zinc acetylacetonate | + | — |
| Zinc salicylate | ± | — |
| Copper sulfate | + + | + |
| Ferrous sulfate | — | — |
| Cobalt chloride | — | — |
| Ammonium molybdate | ± | — |

Figure 5:
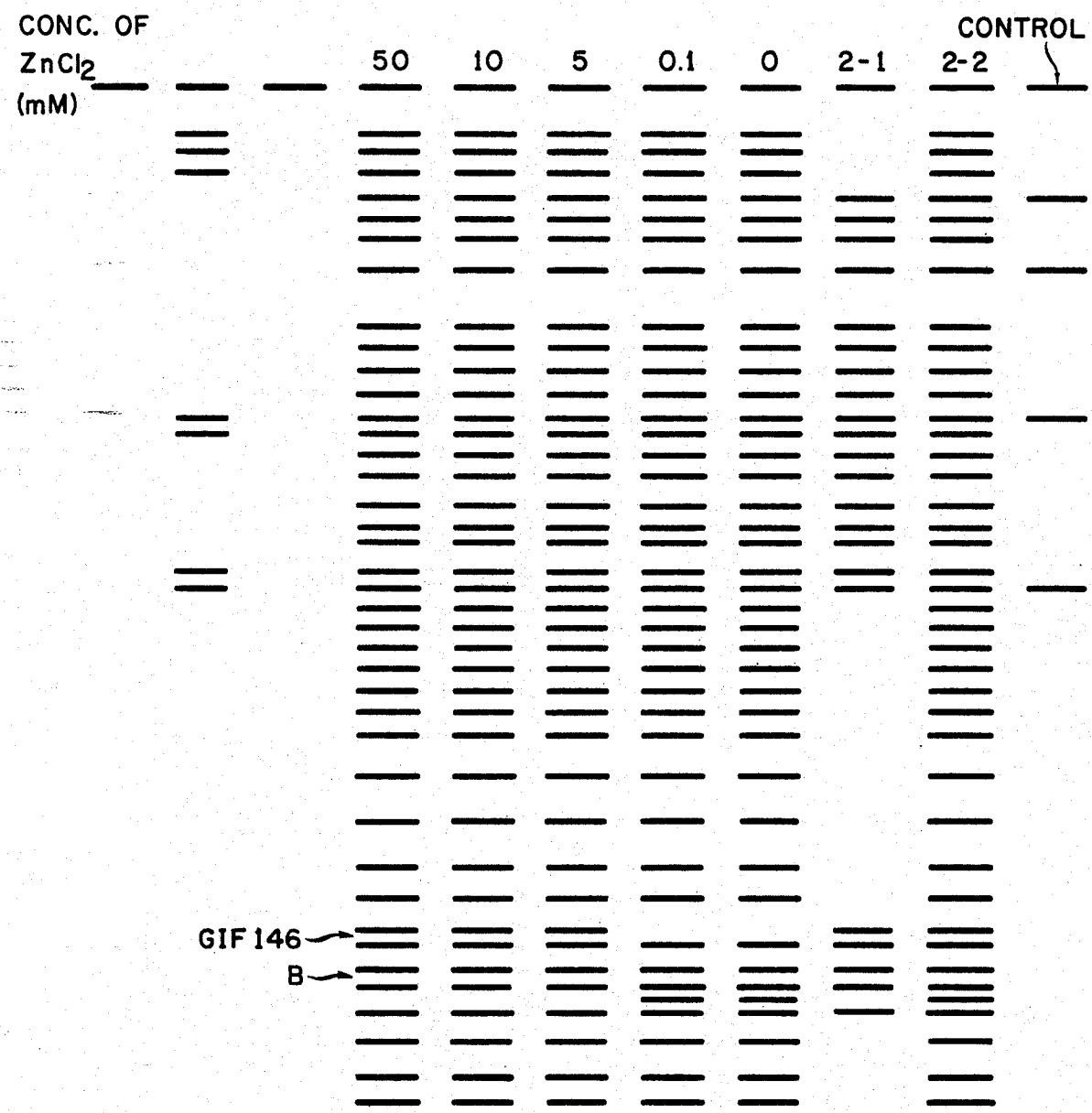
FIG. 5 is a photograph which shows the protein bands of SDS-PAGE obtained by disrupting the cells (W3110/pIN5T4N146) in a buffer solution containing a different concentration of zinc chloride and subjecting the supernatant to SDS-PAGE.
Figure 6:
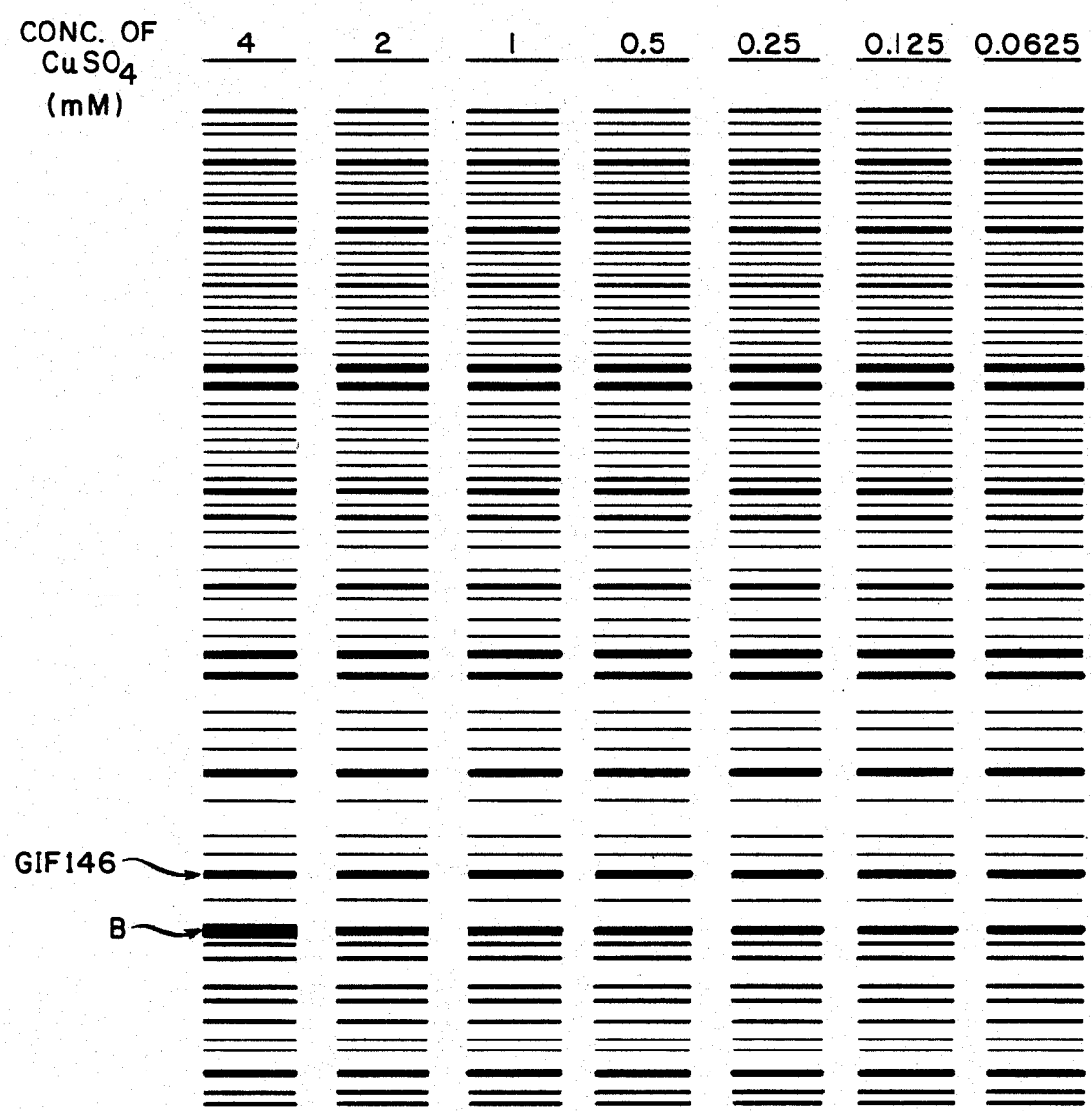
FIG. 6 is a photograph which shows the protein bands of SDS-PAGE obtained by using copper sulfate in the place of zinc chloride.

+ having decomposition-inhibiting effect
− not having decomposition-inhibiting effect FIG. 5 (photograph) is an SDS-PAGE pattern showing the stability of the polypeptide having h-IFN-γ activity (the band of the protein shown by an rrow marked as GIF146 in the figure). The test samples were prepared by disrupting the cells in a desired buffer containing a different concentration of zinc chloride. In FIG. 5 it can be seen that the polypeptide exhibiting h-IFN-γ activity is stable in the presence of 0.5 mM—2 mM of zinc chloride and susceptible to decomposition in the absence or a lower concentration of zinc chloride. The band of the protein shown by arrow "B" shows the polypeptide obtained by decomposition of GIF146 with protease during course of purification. The sample shown by 2-1 was prepared by the treatment described above by using 2 mM of $ZnCl_2$ and then further proceeding purification. Furthermore, the sample shown by 2-2 was prepared by proceeding the purification after the treatment without using $ZnCl_2$. The results of a similar experimental run in which copper sulfate was used instead of zinc chloride are shown in FIG. 6 (photograph). In this case, the desired results are observed in the range of 0.1 mM–4 mM. Although these salts show sufficient protease inhibition with higher concentrations, they are preferably used in as low a concentration as possible because of the necessity to remove them in the purification process. It is preferable that zinc chloride is used in the range of 1–3 mM and copper sulfate in the range of 0.25–1 mM.

Figure 7:
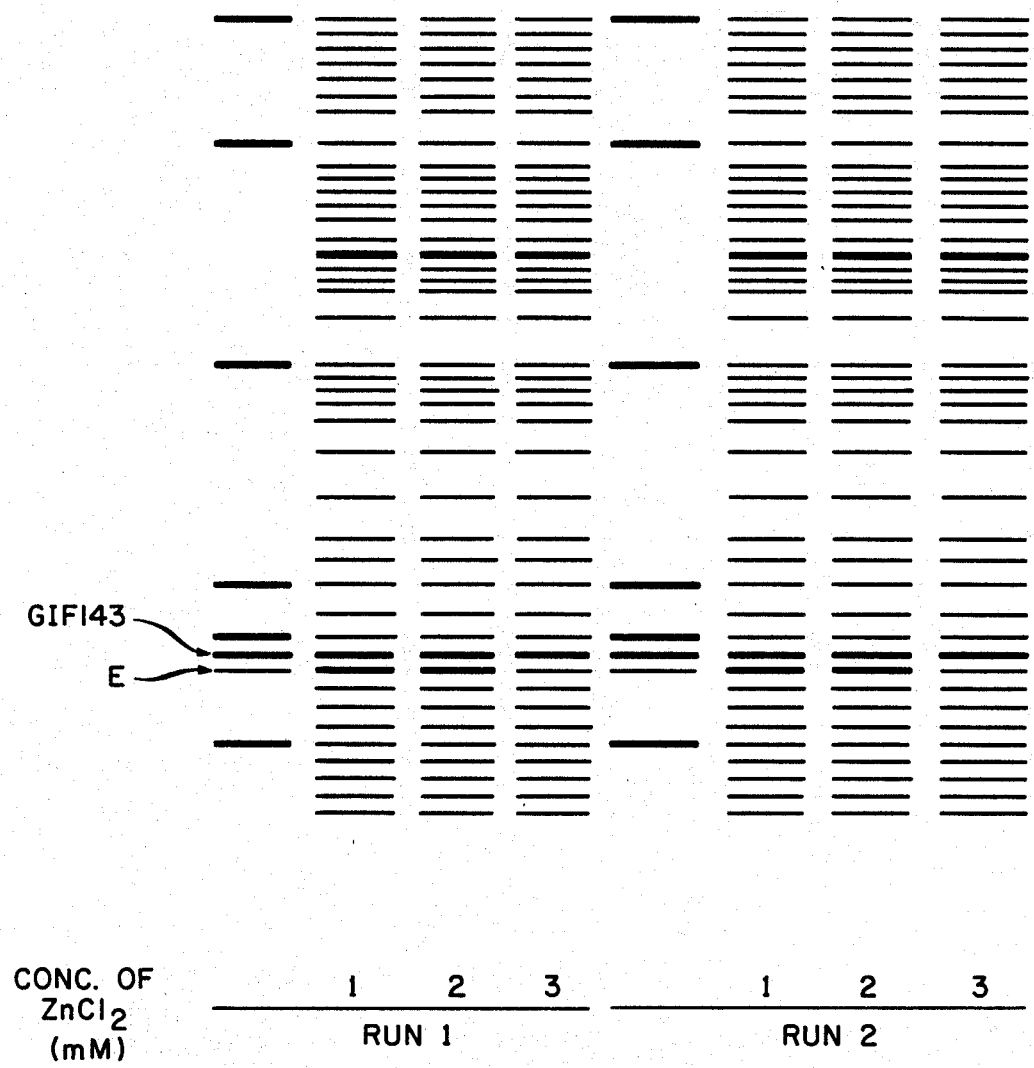
FIG. 7 is a photograph which shows the protein bands of SDS-PAGE obtained by disrupting the cells (W3110/pIN5T4N143) in a buffer solution containing a different concentration of zinc chloride and subjecting the supernatant to SDS-PAGE.

FIG. 7 (photograph) was obtained with respect to a sample prepared by treating GIF143-producing bacteria in the same manner as for FIG. 5. In the figure, the band of the protein shown by an arrow indicated as GIF143 is the polypeptide having h-IFN-γ activity and "E" shows the polypeptide obtained by partially decomposing GIF143 with protease.

The primary classes of contaminants in the disrupted cell/gamma interferon mixture are small-size particulate matter and water-soluble fractions such as nucleic acids, proteases, cell proteins, carbohydrates, lipids, cleaved interferon fragments and interferon aggregates and other fragments resulting from disruption of the cell in which the interferon was produced. We have now discovered that gamma interferon can be obtained in high purity, with the retention of biological activity and with good yields, by processing the interferon-containing mixtures in a specific sequence as described below to minimize degradation of the interferon and to remove the contaminants from the interferon-containing mixture in a defined order.

Substantially improved purity and activity are obtained by removing the contaminants in the interferon-containing mixture in the following order:
(1) nucleic acids;
(2) negatively charged proteases and contaminating cell proteins;
(3) positively charged proteases and contaminating cell proteins; and
(4) cleaved and aggregated interferon.

This sequence of steps is critical to obtaining the desired results of this invention. Provided that the listed contaminants are removed in the specified sequence, additional steps may be used to remove other contaminating materials such as high molecular weight hydrophobic materials, if present. These other materials may conveniently be removed either after step 3 or after step 4.

There are numerous methods, known to the art, to accomplish each of these separations. As stated above, those methods which can accomplish the separations under the mildest conditions, to minimize degradation of the interferon, are the most desirable.

We have found that a preferred method is to use an initial polyethyleneimine precipitation followed by several chromatographic separations to remove the contaminants in the order sepcified above. The resins used in the chromatographic separations and the order of their use is as follows:
(1) anion exchange resin;
(2) cation exchange resin; and
(3) molecular sieve.

In addition to the chromatographic separations, it is useful to employ precipitation, filtration, concentration and dialysis procedures.

In a preferred procedure the gamma interferon-containing mixture is subjected to the following procedures:
(1) nucleic acid removal using polyethyleneimine precipitation;
(2) negatively charged protease and contaminating cell protein removal using weakly basic anion exchange resin;
(3) positively charged protease and contaminating cell protein removal using weakly acidic cation exchange resin; and
(4) cleaved and aggregated interferon and cell fragment removal using a molecular sieve.

Filtration after each step, concentration after steps 3 and/or 4 and dialysis after step 5, are useful adjunctive procedures.

This novel procedure has consistently produced gamma interferon having a purity of at least 95% and a yield in excess of 5%.

An important feature of the present invention is the novel purification scheme, which is suitable for use with gamma interferon produced in any one of a number of ways such as from human cells grown in tissue culture, from leukocytes collected from blood samples or through cloning techniques well known in the art. The purification scheme is particularly well suited for the purification of recombinant gamma interferon recovered from *E. coli* cells. The cells are inactivated by one of the standard methods, such as by the addition of a chemical kill agent such as chlorhexidine gluconate. The inactivated cells are centrifuged, resuspended in a buffer and homogenized. A convenient method for homogenization of the gamma interferon-containing cells is high shear disruption using a Manton-Gaulin homogenizer. The components of the disrupted cells are separated by centrifugation into a precipitate and supernatant. The supernatant from this process is a suitable source for gamma interferon to be isolated and purified by the method described herein.

The suspension of the lysed cells comprises proteins, lipids, carbohydrates and nucleic acids and insoluble cellular debris. Using conventional procedures, the water-insoluble components are separated from the water-soluble fraction of the cell which remains in the supernatant.

It is sometimes desirable to provide certain preliminary processing steps prior to the extraction of the gamma interferon from the cells, such as procedures to minimize degradation of the interferon during processing. Any such preliminary processing steps may be used provided they do not interfere with the purification scheme described herein.

The multistep purification scheme achieves superior yields of pure interferon while maintaining biological activity. The sequence of separation steps is highly significant and is critical to achieving the desirable results disclosed.

The order of removal of the contaminants from the interferon-containing mixture is as follows:
(a) removal of nucleic acids;
(b) removal of negatively charged proteases contaminating cell protein;
(c) removal of positively charged proteases and contaminating cell protein;
(d) removal of low and high molecular weight impurities, cleaved interferon and interferon aggregates.

For reasons presently unknown, removal of impurities in the order stated is critical to achieving high yields of purified gamma interferon with retention of biological activity. The individual steps used for the removal of each class of impurities are conventional and known to the art. Due to the tendency of the gamma interferon to cleave or aggregate into inactive forms under harsh processing conditions, purifications steps which can be conducted under the mildest processing conditions are preferred.

The invention is further described utilizing specific processing steps and conditions which have been found to minimize degradation of the interferon, but it should be recognized that other conventional processing steps may be substituted for those disclosed provided that the sequence of impurity removal remains as described.

Unless otherwise stated in the following description, pH values given may generally vary ±0.5, preferably in the range ±0.25 and most preferably ±0.1. Conductivity measurements may generally vary ±5 mS, and are preferably held in the range ±3 mS. Operations are performed at a temperature in the range of from about 2° to about 15° C.

The first step of the processing scheme involves the removal of nucleic acids. This removal is conveniently accomplished by adding polyethyleneimine to the supernatant from the centrifuged mixture of lysed gamma interferon-containing cells. Alternatively, the polyethyleneimine solution may be added prior to homogenization of the cells, if desired. The polyethyleneimine is added slowly with stirring to a maximum concentration of about 0.8% and the mixture is allowed to settle for an appropriate period, generally in the range of from about 30 to about 90 minutes. The mixture is then centrifuged and the supernatant collected. Excellent results are obtained when the polyethyleneimine is added as a 10% (v/v) solution in $H_2O$ in amount sufficient to result in the polyethyleneimine consisting of from about 0.7 to about 0.8% (v/v) of the total solution. The pH of the solution is 8±0.5, preferably ±0.1 and the temperature is held in the range of from about 2° to about 15° C. The protein concentration in the supernatant is determined at this stage and at each further processing stage by the standard Coomassie blue binding assay.

Another procedure for removal of the nucleic acid is by using chromatography on hydroxyapatite or immobilized PEI. Precipitation with protamine sulfate is another useful procedure.

After removal of the nucleic acids, the gamma interferon-containing mixture is subjected to a first protease removal step. The most convenient method for removing the proteases is by chromatography of the supernatant from the nucleic acid removal step utilizing an anion exchange resin. Quaternary aminoethyl, mixed amine or other intermediate base resin or a weak base resin such as p-amino benzyl cellulose is particularly useful.

Quaternary aminoethyl is a preferred anion exchange resin. The quaternary aminoethyl may be attached to a cross-linked dextran, cellulose, agarose or acrylic support. The pH of the supernatant liquid is adjusted to 8.7±0.5, preferably ±0.1, utilizing sodium hydroxide or any other convenient base. The conductivity of the solution is adjusted to below 10 mS, preferably in the range of from about 4 to about 8 mS, by the addition of deionized $H_2O$.

The elution buffer comprises 20 mM sodium 4-(2-hydroxyethyl)-1-piperazine-propane sulfonate and 0.1% (v/v) 2-mercaptoethanol. The pH of the buffer is adjusted to approximately 8.7 with sodium hydroxide or other base. Other buffers suitable for use in the same pH range may be substituted for the piperazine derivative and other antioxidants may be substituted for the mercaptoethanol.

The quaternary aminoethyl column is pre-equilibrated with the buffer solution, the gamma interferon-containing solution is added and the adsorbed material eluted with the same buffer. Approximately the first two-thirds of the eluted protein solution, i.e., the first two-thirds of the volume, is pooled for transfer to the next purification step. The remaining one-third of the eluate may be rechromatographed on the same column equilibrated in the same manner. Approximately the first two-thirds of the protein flow-through is again pooled. The remaining solution may be further processed in the same manner. As previously, the protein concentration is determined by a Coomassie blue binding assay.

An optional concentraton step may be employed at this point in the purification. One convenient method of concentrating the solution is precipitation with ammonium sulfate. The eluate from the quaternary aminoethyl column is passed through a 0.2μ filter and ammonium sulfate is added to a final concentration of from about 40 to about 60% saturation, with stirring, over a 5-10 minute period. The suspension is allowed to stand for several hours in an ice bath. The precipitate is then collected by centrifugation and may be stored at approximately −20° C. until required for further processing.

When required, the precipitate is dissolved in a solution comprising 20 mM Tris-HCl and 0.1% 2-mercaptoethanol at a pH of approximately 7.5 that has been previously passed through a 10,000 molecular weight cut-off filter. The conductivity of the solution is lowered to from about 3 to about 5 mS by the addition of a solution comprising 10 mM Tris-HCl and 0.1% 2-mercaptoethanol at a pH of approximately 7.5. The solution is passed through a 0.2μ filter and is ready for further processing. Other buffers suitable for use in the same pH range may be substituted for the Tris-HCl and other antioxidants may be substituted for the mercaptoethanol.

The positively charged proteases and other proteins in the solution are removed in the next processing step, which is conveniently accomplished utilizing a cation exchange resin.

Excellent results have been obtained using a carboxymethyl cation exchange resin (carboxymethyl) attached to cross-linked dextran, cellulose, agarose or acrylic support). The pH of the solution from the previous process step is adjusted to about 7.5 utilizing HCl or other appropriate acid. 2-Mercaptoethanol or other suitable antioxidant is added to a concentration of about 0.1% (v/v). Deionized water containing 0.1% (v/v) 2-mercaptoethanol is also added to reduce the conductivity to below 20 mS, preferably to the range of about 3-5 mS. The solution is filtered through a 0.2 micron filter in preparation for subsequent chromatography.

The cation exchange resin column is equilibrated with a suitable buffer such as a solution comprising 20 mM Tris-HCl and 0.1% 2-mercaptoethanol at a pH of approximately 7.5. After column equilibration by washsing the column two or three times with the equilibrating buffer and addition of the gamma interferon-containing solution, the solution is eluted with approximately 13 to 15 column volumes of a gradient of sodium chloride dissolved in the equilibrating buffer. The sodium chloride content is increased from 0 to a maximum of approximately 0.5M in the buffer.

Appropriate fractions are collected and may be analyzed by gel electrophoresis (SDS-PAGE), analytical HPLC and antiviral activity. The purest fractions are pooled for further processing. The fractions containing interferon of lower purity may be precipitated with approximately 40 to 60% saturation ammonium sulfate, redissolved, filtered and rechromatographed on a carboxymethyl column as previously described. Fractions collected from the rechromatographed solution are analyzed and the purest fractions pooled with the fractions obtained from the first carboxy-methyl elution.

If the presence of high molecular weight hydrophobic impurity is detected by SDS-PAGE or other appropriate procedure, the eluate is subjected to optional chromatography to remove such impurities at this stage in the purification process. A phenyl resin has been found to provide satisfactory results. Octyl and butyl resins may also be used. The solution from the previous processing step is filtered through a 0.2μ filter and sodium chloride added (0.5–0.75M) to raise the conductivity of the solution to approximately 50 to 75 mS.

The buffer is a solution comprising 20 mM Tris-HCl, 0.1% (v/v) 2-mercaptoethanol and 50 to 850 mM, preferably 500 to 700 mM, sodium chloride or other salt to increase the conductivity to the appropriate range.

The column is pre-equilibrated with the buffer and the sample is loaded onto the column. From about 2 to about 4 column volumes of the buffer solution are added to the column. The adsorbed material is then eluted with at least one and preferably from about 5 to about 10 column volumes of a solution comprising 20 mM Tris-HCl, 100 mM NaCl and 0.1% (v/v) 2-mercaptoethanol at a pH of approximately 7.5. Appropriately sized fractions are collected and analyzed using SDS-PAGE, analytical HPLC and antiviral activity. The purest fractions are pooled.

It is generally desirable to concentrate the interferon-containing solution after the phenyl-column chromatography. It is also generally desirable to concentrate the interferon-containing solution at this stage in those instances where the optional hydrophobic column chromatography step has not been utilized.

The protein concentration of the solution is determined by the Coomassie blue binding assay. If the protein concentration is determined to be less than 0.2 mg/ml, the solution is preferably concentrated by ultrafiltration employing a 10,000 molecular weight cut-off membrane.

Further concentration may be accomplished by adding ammonium sulfate to the solution to a final ammonium sulfate concentration of from about 40 to about 60% saturation with stirring over a 5 to 10 minute period. The suspension is allowed to stand in an ice bath after which the precipitate is collected by centrifugation. The precipitate is redissolved in a solution comprising 20 mM Tris-HCl, 500 mM sodium chloride and 0.1% 2-mercaptoethanol at a pH of about 7.5 that has been previously filtered through a 10,000 molecular weight cut-off filter. The concentrated solution is passed through a 0.2μ filter in preparation for the next purification step.

Low and high molecular weight impurities and cleaved gamma interferon and interferon aggregates are removed in a final chromatographic purification step by passing the gamma interferon-containing solution from the previous processing step through a gel filtration resin. The hydrophilic filtration gel acts as a molecular sieve to separate appropriate sized fractions from high and low molecular weight impurities contained in the solution. A particularly useful filtration gel is a cross-linked dextran based gel, identified by the trademark SEPHADEX G-100, manufactured by Pharmacia Fine Chemicals. The resin has a fractionation molecular weight range of 4,000 to 150,000 for globular protein and peptides and 1,000 to 100,000 for polysaccharides. Other resins having cut-off ranges of from about 1,000 to about 200,000 for proteins may also be used.

The SEPHADEX G-100 resin column is pre-equilibrated with a buffer solution comprising 20 mM Tris-HCl, 500 mM NaCl and 0.1% 2-mercaptoethanol at a pH of approximately 7.5. The adsorbed material is eluted with the buffer and appropriate fractions collected. The protein concentration of each fraction is determined by a Coomassie blue binding assay. The fractions are combined on the basis of purity as judged by SDS-PAGE, analytical HPLC and antiviral activity.

Alternatively, the precipitate from the ammonium sulfate concentration step may be dissolved in a buffer solution of 20 mM sodium phosphate, 500 mM sodium chloride and 0.1% (v/v) 2-mercaptoethanol at a pH of about 7.5. The gamma interferon-containing solution is charged to a SEPHACRYL S-200 gel filtration column, preequilibrated with the same buffer (SEPHACRYL S-200 is a trademark of Pharmacia Fine Chemicals for a resin of agarose cross-linked with acrylamide). The final product is a clear to slightly hazy solution, colorless to light yellow in color. The apparent molecular weight determined by SDS-PAGE is in the range of 17,000 to 19,500.

The purified gamma interferon is dialysed against a buffer before use. A suitable buffer comprises 20 mM sodium phosphate and 6 mM L-cysteine at a pH of about 6.8. Another suitable buffer is 15 mM sodium phosphate, 8 mM sodium citrate and 6 mM L-cysteine HCl at a pH of 5.0. It is preferable to continue to dialyse for 8 hours or more and to continuously flush nitrogen through the system to minimize oxidation.

If necessary, the purified gamma interferon solution can be concentrated in the manner described above.

The present invention will now be explained with reference to the reference example and the working example 1–3.

REFERENCE EXAMPLE: (CONSTRUCTION OF GIF143 EXPRESSION VECTOR)

A GIF143 expression vector was produced according to the following procedures.

pGIF54 (a plasmid equivalent to pGIF4 bearing a gene coding for GIF146) was obtained from WA802/pGIF54 which was a dcm *Escherichia coli* transformant (a strain lacking methylation of cytosine) according to a conventional method. pGIF54 (5 μg) was treated with 20 units of AatII and 20 units of BglII to obtain a DNA fragment of about 600 base pairs bearing a part of GIF146 gene and a lac UV5 promoter. Then, 0.5 μg of the DNA fragment was cleaved by using 5 units of AvaII to obtain the fragment of about 400 base pairs bearing a part of GIF146 gene. On the other hand, 5 μg of pIN5T4 was digested by using 20 units of EcoRI and 20 units of BglII to obtain the DNA fragment bearing a tetracycline-resistant gene, lpp promoter, and a replication initiation site. Both the DNA fragment and 0.5 μg of the chemically-synthesized linker shown in in FIG. 1 (synthesized by using a DNA synthesizer; Applied Biosystems 380A) were subjected to mixed-ligation to obtain pIN5GN143. W3110 was transformed by the obtained pIN5T4N143 by a conventional method, for example, the method described in Japanese Patent Public Disclosure No. 63395/1983, to obtain W3110/pIN5T4N143.

It was confirmed that the obtained transformant was a GIF143-producing strain by the following procedures.

W3110/pIN5T4N143 was cultivated with shaking in 1.5 ml of a medium containing polypeptone 3%, yeast extract 2%, glucose 2%, $KH_2PO_4$ 0.5%, $MgSO_4 \cdot 7H_2O$ 0.010% and tetracycline 20 μg/ml in a 16.5 mm test tube at 30° C. ($OD_{660}=8$), 0.5 ml of the culture mixture was transferred to an Eppendorf cup of 1.5 ml and centrifuged to collect the cells (10,000 rpm, for 5 minutes). The cells were suspended in 0.5 ml of PBS solution (0.8% NaCl, 0.02% KCl, 0.115% $Na_2HPO_4$, 0.02%

NaH$_2$PO$_4$) containing 1 mg/ml lysozyme 1 mM-EDTA and reacted at 0° C. for 30 minutes. The cells were then disrupted by repeating freeze-thawing treatment 3 times and the supernatant fraction was recovered by centrifugation (10,000 rpm, for 10 minutes). The supernatant fraction was investigated for anti-virus activity according to the method described in Japanese Patent Public Disclosure No. 201995/1983. As a result, an anti-virus activity of 6×10$^4$ units/ml was recognized. On the other hand, the cells obtained by collection in the same manner as before were dissolved in 200 μl of an SDS sample solution (10 mM phosphate buffer solution containing 7M urea, 1% SDS, 1% 2-mercaptoethanol, pH 7.2) and then heated on a boiling water bath for 10 minutes. The resulting sample (20 μl) was isolated by 13% SDS-PAGE and subjected to protein staining with Coomascie blue R250 As a result, it was confirmed that GIF143 protein (about 18 kd molecular weight) in a yield corresponding to about 20% of the total protein of *Escherichia coli* was produced.

EXAMPLE 1

Extraction and Purification of GIF146

W3110/pIN5T4 which was a GIF146 producing strain was cultured with aerating and shaking in a medium containing 3% polypeptone, 2% yeast extract, 2% glucose, 0.5% KH$_2$PO$_4$, 0.01% MgSO$_4$ 7H$_2$O and 20 μg/ml tetracycline for 24 hours. The cells of the culture mixture were completely killed with chlorohexidine gluconate and centrifuged (8,000 rpm, for 10 minutes) to obtain 800 g of the W3110/pIN5T4 wet cells. They were suspended in 5.1 liters of a cooled 20 mM tris-HCl buffer (abbreviated to "THB" hereinafter) having pH of 7.4 and containing 1 mM ZnCl$_2$, disrupted by subjecting them to homogenizer M15 (manufactured by Manton Gaulin Co., Ltd.), cooled with ice and then centrifuged (7,000 rpm, for 20 minutes) to obtain the supernatant. To the supernatant was added an aqueous 15% solution of polyethyleneimine (abbreviated to "PEI" hereinafter) having a pH of 8.0 adjusted with HCl so as to achieve a final concentration of 0.75%. The resulting solution was stirred for 10 minutes and was allowed to stand at 4 C for 2 hours. The precipitates produced were removed by centrifugation (7,000 rpm, for 20 minutes) to obtain 4.7 liters of the supernatant. The supernatant was subjected to a QAE Sephadex A-25 (manufactured by Pharmacia Co., Ltd.) column equilibrated with a 20 mM N-2-hydroxyethylpiperazinyl-N'-3-propane sulfonate buffer (EPPS buffer) of pH 8.6 to obtain the non-absorbed fraction. The fraction obtained was then subjected to a CM Sepharose CL6B (manufactured by Pharmacia Co., Ltd.) column equilibrated with 20 mM THB of pH 7.4 containing 0.1% of 2-mercaptoethanol (abbreviated to "2-ME" hereinafter) and the active fraction absorbed on the column was eluted with a linear concentration gradient of 0 to 0.5M NaCl to collect fractions which had a high interferon activity. The interferon activity was measured according to the method described in Japanese Patent Public Disclosure No. 201995/1983. Ammonium sulfate was then added, to the fraction so as to achieve a 50% saturation and salting-out was then carried out, followed by centrifugation at 7,000 rpm for 20 minutes to obtain the precipitate. The precipitate was dissolved in a 20 mM sodium phosphate buffer (abbreviated to "20 mM PBS" hereinafter) of pH 7.4 containing 0.3 NaC and 0.1% 2-ME and subjected to a Sephacryl S-200 (manufactured by Pharmacia Co., Ltd.) column equilibrated with the same buffer solution to obtain 298 mg of the polypeptide corresponding to GIF146 as a final purified product (the specific activity of interferon: 1.6–1.7×10$^6$/mg). Analysis of the polypeptide by SDS-PAGE showed more than 99% purity and the position of the band by the same SDS-PAGE was in agreement with that of GIF146 which was not decomposed. Furthermore, it was confirmed that the polypeptide obtained had the same amino acid sequence as the amino acid sequence (I) by an amino acid analysis. This shows the usefulness of the purification method of the present invention.

When Sephadex G-100 (manufactured by Pharmacia Co., Ltd.) was employed instead of Sephacryl S-200 used in the previously described purification processes, similar results were obtained.

EXAMPLE 2

Purification and extraction of GIF143

In the same manner as described in Example 1, W3110/pIN5T4N143 (refer to the Reference Example) was cultured, and the cells were killed with chlorohexidine gluconate, and collected. The wet cells (300 g) were suspended in 2.1 liters of a 20 mM THB (pH 7.4) containing 3 mM ZnCl$_2$ and disrupted by homogenization, followed by centrifugation (7,000 rpm for 20 minutes) to obtain the supernatant. It was treated with PEI in the same manner as in Example 1 to obtain 1,000 ml of the supernatant. The liquid was then absorbed on a CM Sepharose CL6B column equilibrated with 20 mM THB (pH 7.4) containing 0.1% 2-ME and eluted by a linear concentration gradient of 0.1–0.8M NaCl. The active fraction was diluted to 10-fold of the original volume with 20 mM THB containing 0.1% of 2-ME, absorbed on a CM-Toyopearl column (manufactured by Toyo Soda Co., Ltd.) which had been equilibrated with the same buffer solution, wasted and then eluted with a linear concentration gradient of 0.1–0.8M NaCl. The fractions having interferon activity were collected, and after ammonium sulfate was added to the combined fractions so as to achieve a 20% saturation, passed through a Butyl Toyopearl column (manufactured by Toyo Soda Co., Ltd.). The fractions passed through the column were collected and subjected to dialysis against distilled water to give 396 mg of protein as a final product (interferon specific activity: 4.8×10$^6$ U/mg protein).

As a result of the amino acid analysis and SDS-PAGE as described in Example 1, it was found that the obtained polypeptide (GIF143) had a purity of more than 99% and had the same amino acid sequence as the above-described amino acid sequence (III). Furthermore, none of the zinc compound added during the extraction step could be detected even by atomic absorption spectrophotometry.

EXAMPLE 3

I. Cell Harvest, Protein Release and Polyethyleneimine Precipitation

Inactivated *E. coli* (W3110/pIN5T4) cells containing recombinant gamma interferon are collected by centrifugation. Cells are resuspended in 20 mM Tri-HCl buffer (pH 7.5) containing 1 mM ZnCl$_2$. The cells are disrupted in a high pressure homogenizer. The cell homogenate is centrifuged and the supernatant is collected. An aqueous 10% (v/v) polyethyleneimine (PEI) solution adjusted to pH 8 with hydrochloric acid is added to the supernatant to bring the final PEI concentration to a maximum of 0.8%. The mixture is centrifuged and the supernatant is collected.

II. Quaternary Aminoethyl (QAE) Column Chromatography

The pH of the PEI supernatant is adjusted to 8.7 with 4N NaOH. Deionized water is added to reduce the conductivity to below 10 mS. The batch is applied onto a QAE column at a loading of not greater than 50 grams of protein per liter of gel. The column is equilibrated with a buffer of 20 mM sodium 4-(2-hydroxyethyl)-1-piperazine-propane sulfonate and 0.1% 2-mercaptoethanol at a pH of 8.7 prior to loading. Elution is performed with the same buffer. The protein solution is collected and chromatographed in Stage III.

III. Carboxymethyl (CM) Column Chromatography

The pH of the protein eluate from Step 2 is adjusted to 7.5 with 4N HCl and 2-mercaptoethanol is added to a final concentration of 0.1%. The conductivity is adjusted to 20 mS or below by diluting with ultrafiltered water containing 0.1% 2-mercaptoethanol. The solution is passed through a 0.2$\mu$ filter and charged onto a CM column at a loading of not greater than 35 grams of protein per liter of gel. The column is equilibrated with a buffer of 20 mM Tris-HCl and 0.1% 2-mercaptoethanol at a pH of 7.5 adjusted to a conductivity of 20 mS or below with sodium chloride prior to loading. The column is washed with at least 2 column volumes of the equilibrating buffer. The gamma interferon is eluted with a salt gradient in the range of 0–0.5M NaCl dissolved in the equilibrating buffer. Fractions are combined as determined by sodium dodecyl sulfate-polyacrylamide gel electrophoresis (SDS-PAGE).

IV. Phenyl Column Chromatography

Chromatography on a phenyl column is performed after the presence of higher molecular weight impurities is detected by SDS-PAGE. Sodium chloride is added to bring the conductivity to 50–75 mS before the solution is charged onto a phenyl column at a loading of not greater than 15 grams of protein per liter of gel. The column is equlibrated with a buffer of 20 mM Tris-HCl, 0.5M NaCl, 0.1% 2-mercaptoethanol at a pH of 7.5 prior to loading. After the sample is loaded onto the column, it is followed by at least one bed volume of equlibrating buffer. The column is eluted with 20 mM Tris-HCl, 0.15M NaCl, 0.1% 2-mercaptoethanol at a pH of 7.5. Active fractions are combined as determined by SDS-PAGE and antiviral assay.

V. Ammonium Sulfate Precipitation

If the protein concentration of the combined carboxymethyl (Step III) or phenyl (Step IV) fractions is less than 0.2 mg/ml, the solution is concentrated by ultrafiltration employing a 10,000 M.W. cut-off membrane. Ammonium sulfate is added to a final concentration of 40 to 60% saturation. The precipitate is collected by centrifugation and stored at about −20° C., if required.

VI Sephadex G-100 Column Chromatography

The ammonium sulfate precipitate is dissolved in a buffer of 20 mM Tris-HCl, 0.5M NaCl, 0.1% 2-mercaptoethanol at a pH of 7.5. The solution is centrifuged prior to passing through a 0.2$\mu$ filter. The filtered solution is charged onto a Sephadex G-100 column pre-equilibrated with the same buffer. The loading is not greater than 3.5 grams of protein per liter of gel. The column is eluted with the same buffer and fractions are combined as determined by SDS-PAGE.

VII. Purified Gamma Interferon Dialysis

The combined Sephadex G-100 fractions are dialyzed against 15 mM sodium phosphate, 8 mM sodium citrate, 6 mM L-cysteine HCl at a pH of 5.0. Dialysis is carried out with continuous sparging of nitrogen through the buffer with two changes of buffer at a minimum of five hour intervals. If necessary, the dialyzed solution is concentrated by ultrafiltration using a 10,000 molecular weight cut-off membrane to a protein concentration greater than 1 mg/ml. The solution of purified gamma interferon is passed through a 0.2$\mu$ filter and stored at about −20° C. or below.

The purified gamma interferon may be stored for at least several months at temperatures of approximately −20° C. to about −30° C. by adding 50% glycerol to the gamma interferon-containing solution.

The gamma interferon is prepared for use by filtering through a 0.2$\mu$ filter and dialyzing the solution against a solution comprising 20 mM sodium phosphate and 6 mM L-cysteine at a pH of about 6.8. Alternatively, the dialysis solution is 15 mM sodium phosphate, 8 mM sodium citrate and 6 mM L-cysteine HCl, at a pH of about 5. After a dialysis period of at least 8 hours carried out under continuous nitrogen sparging, the solution is preferably filtered through a 10,000 molecular weight cut-off filter.

Product obtained has a purity of at least 95% gamma interferon and a yield in excess of approximately 5%.

We claim:

1. A method of purifying gamma interferon from a culture mixture of a microorganism obtained by a recombinant DNA technique and capable of producing gamma interferon, wherein a zinc salt or copper salt and polyethyleneimine are added during a step of extraction or purification of gamma interferon.

2. A method according to claim 1, wherein the microorganism cells recovered from the culture mixture of the microorganism capable of producing gamma interferon are suspended in a solution containing a zinc salt or copper salt, and disrupted, and polyethyleneimine is added to the supernatant obtained by centrifugation of the suspension of the disrupted cells.

3. A method according to claim 1 wherein said gamma interferon is human gamma interferon.

4. A method according to claim 2 wherein said zinc salt is added in such an amount that the concentration thereof is in the range from 0.5 mM to 5 mM; or said copper salt is added in such an amount that the concentration thereof is in the range from 0.05 mM to 3 mM; and polyethyleneimine is added in such an amount that the concentration thereof is in the range from 0.5 to 1.5%.

5. A method of claim 2 which comprises the further steps of sequentially removing negatively charged contaminating proteins; removing positively charged contaminating proteins; and removing low and high molecular weight materials from the gamma interferon-containing solution by the steps of sequentially removing
    (1) negatively charged contaminating proteins by column chromatography with a weak base anion exchange resin;

(2) positively charged contaminating proteins by column chromatography with a weak acid cation exchange resin;

(3) low and high molecular weight materials by permeation chromatography with a gel filtration resin.

6. The method of claim 5 where the process includes the additional step of removing high molecular weight hydrophobic materials from the gamma interferon-containing solution either immediately after removal of the positively charged proteins or immediately after removal of the low and high molecular weight materials.

7. The method of claim 5 wherein the anion exchange resin is a quaternary aminoethyl resin.

8. The method of claim 5 wherein the weak acid cation exchange resin is a carboxymethyl resin.

9. The method of claim 5 wherein the filtration gel is a cross-linked dextran based gel or a resin of agarose cross-linked with acrylamide.

10. The method of claim 9 wherein the anion exchange resin is a quaternary aminoethyl resin and the weak acid cation exchange resin is a carboxymethyl resin.

11. The method of claim 5 further comprising concentration of the gamma interferon-containing solution after step 1, after step 2, or after each of step 1 and step 2, wherein the gamma interferon-containing solution is concentrated by ultrafiltration, by precipitation with ammonium sulfate, or by ultrafiltration followed by precipitation with ammonium sulfate.

12. The method of claim 10 further comprising the concentration of the gamma interferon-containing solution after anion exchange, after cation exchange, or after each of anion exchange and cation exchange by ultrafiltration, by precipitation with ammonium sulfate, or by ultrafiltration followed by precipitation with ammonium sulfate.

13. The method of claim 5 where the process includes a final step of dialysis against cysteine-containing buffer in an oxygen-free environment of the gamma interferon-containing solution.

14. A method of claim 2 comprising the further steps of:

(1) centrifuging the mixture containing polyethyleneimine and zinc or copper salt to separate the resulting precipitate from the supernatant solution;

(2) adsorbing the solution from step 1 on a column containing an anion exchange resin;

(3) eluting the adsorbing material;

(4) adsorbing the eluate from step 3 onto a column containing a cation exchange resin;

(5) eluting the adsorbed material;

(6) adsorbing the eluate from step 5 onto a column containing a gel filtration resin; and (7) eluting the adsorbed material.

15. The method of claim 14 wherein the material adsorbed on the anion exchange resin is eluted with a buffer comprising sodium 4-(2-hydroxyethyl)-1-piperazine-propane sulfonate and 2-mercaptoethanol.

16. The method of claim 14 wherein the material adsorbed on the cation exchange resin is eluted with a buffer comprising Tris-HCl and an antioxidant.

17. The method of claim 14 wherein the material adsorbed on the gel filtration resin is eluted with a buffer comprising Tris-HCl.

18. The method of claim 15 wherein the material adsorbed on the cation exchange resin is eluted with a buffer comprising Tris-HCl and an antioxidant and wherein the material adsorbed on the gel filtration resin is eluted with a buffer comprising Tris-HCl.

19. The method of claim 18 wherein the anion exchange resin is a quaternary aminoethyl resin; the cation exchange resin is a carboxymethyl resin; and the gel filtration resin is Sephadex G-100.

20. A method according to claim 3 wherein the human immune interferon is GIF146 or GIF143.

21. The method of claim 12 wherein the process includes a final step of dialysis of the gamma interferon-containing solution against cysteine-containing buffer in an oxygen-free environment.

* * * * *